(12) United States Patent
Chun

(10) Patent No.: US 6,619,560 B1
(45) Date of Patent: Sep. 16, 2003

(54) BOTTLE ASSEMBLY WITH WICK HOLDER ASSEMBLY

(75) Inventor: Yip Po Chun, Fo Tan (HK)

(73) Assignee: Blyth, Inc., Greenwhich, CT (US)

( * ) Notice: Subject to any disclaimer, the term of this patent is extended or adjusted under 35 U.S.C. 154(b) by 0 days.

(21) Appl. No.: 10/199,293

(22) Filed: Jul. 19, 2002

(51) Int. Cl.[7] .................... A24F 25/00; A61L 9/04; B65D 39/00; B65D 23/12; B65D 25/00
(52) U.S. Cl. .................... 239/44; 239/50; 239/57; 239/326; 215/227; 215/386; 220/694
(58) Field of Search ............... 239/34, 43, 44, 239/50, 57, 47, 53, 55, 326; 392/395; 215/227, 228, 386; 220/694

(56) References Cited

U.S. PATENT DOCUMENTS

| | | | |
|---|---|---|---|
| 2,176,345 A | 10/1939 | Hurwitt | |
| 3,028,100 A | * 4/1962 | Xenakis et al. | 239/47 |
| 3,091,396 A | * 5/1963 | Curtin | 239/47 |
| 3,724,756 A | 4/1973 | Maltenfort | 239/47 |
| 4,346,059 A | 8/1982 | Spector | 422/125 |
| 4,494,926 A | 1/1985 | Riha | 431/321 |
| 4,621,768 A | 11/1986 | Lhoste et al. | 239/44 |
| 4,739,928 A | 4/1988 | O'Neil | 239/45 |
| 5,038,394 A | 8/1991 | Hasegawa et al. | 392/395 |
| 5,095,647 A | 3/1992 | Zobele et al. | 43/125 |
| 5,622,314 A | 4/1997 | Eason | 239/47 |
| 5,647,053 A | 7/1997 | Schroeder et al. | 392/390 |
| 5,840,246 A | * 11/1998 | Hammons et al. | 422/4 |
| 5,903,710 A | 5/1999 | Wefler et al. | 392/392 |
| 5,906,298 A | * 5/1999 | Ward | 222/175 |
| 5,909,845 A | 6/1999 | Greatbatch et al. | 239/44 |
| 5,945,094 A | 8/1999 | Martin et al. | 424/76.1 |
| 5,976,503 A | 11/1999 | Martin et al. | 424/43 |
| 6,236,807 B1 | 5/2001 | Ruffolo et al. | 392/390 |
| 2002/0076214 A1 | 6/2002 | Vieira | 392/395 |

FOREIGN PATENT DOCUMENTS

| | | |
|---|---|---|
| EP | 0 740 941 | 11/1996 |
| EP | 1 103 479 | 5/2001 |
| GB | 672097 | 5/1952 |
| IT | 477291 | 1/1953 |
| WO | WO 98/19526 | 5/1998 |
| WO | WO 01/39809 | 6/2001 |

* cited by examiner

*Primary Examiner*—Kevin Shaver
*Assistant Examiner*—Anuradha Ramana
(74) *Attorney, Agent, or Firm*—Marshall, Gerstein & Borun

(57) ABSTRACT

A bottle assembly is provided. The bottle assembly includes a bottle having a neck with a neck passage disposed therethrough, and a wick holder assembly disposed in the neck passage and having a wick holder passage disposed therethrough. The wick holder assembly includes at least two fingers, each of the fingers having an inner surface that defines part of the wick holder passage and an outer surface, and a clip disposed abutting the outer surfaces of the at least two fingers. The bottle assembly also includes a wick disposed in the wick holder passage with at least a part of the wick between the at least two fingers. The wick has an outer surface that abuts the inner surface of the wick holder passage with the clip disposed abutting the outer surfaces of the at least two fingers.

20 Claims, 2 Drawing Sheets

BOTTLE ASSEMBLY WITH WICK HOLDER ASSEMBLY

FIELD OF THE DISCLOSURE

This disclosure is directed to a bottle assembly with a bottle and a wick, and, in particular, to a bottle assembly with a bottle, a wick and a holder to limit removal of the wick from the bottle.

BACKGROUND

It is known to provide a fragrance dispersal device including a bottle, a wick and a heater. The bottle is filled with a fragrance solution. The wick has a first end extending from the bottle and a second end disposed in the bottle. The wick uses capillary action to draw the fragrance solution from the second end to the first end. The heater is disposed proximate to the first end of the wick. Heat from the heater evaporates the fragrance solution drawn out of the bottle and disperses it into the surrounding environment.

It is also known to provide a wick holder. The wick is received within the wick holder, and the wick holder is received in a passage in a neck of the bottle. The wick holder may cooperate with a locking device to prevent removal of the wick from the wick holder. For example, a pin may be disposed through the wick below the wick holder, and the cooperation of the pin and the wick holder limits removal of the wick. Alternatively, the wick holder may enclose substantially the entire wick to limit its removal.

DETAILED DESCRIPTION OF THE PREFERRED EXAMPLES

Figure 1:
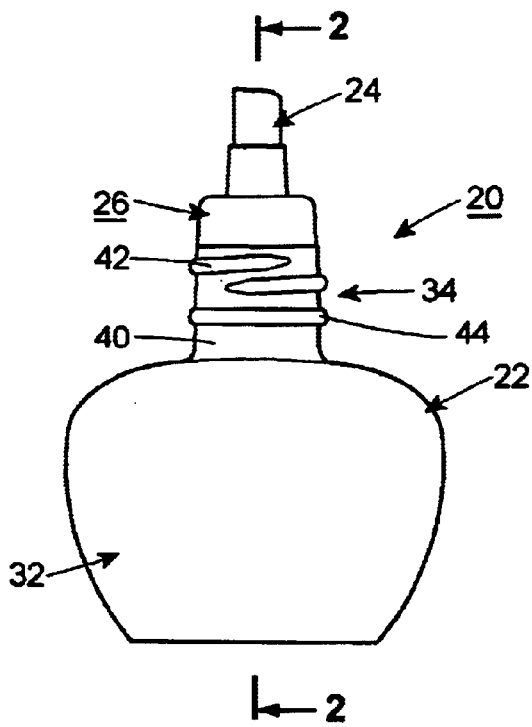
FIG. 1 is a side view of a bottle assembly.
Figure 2:
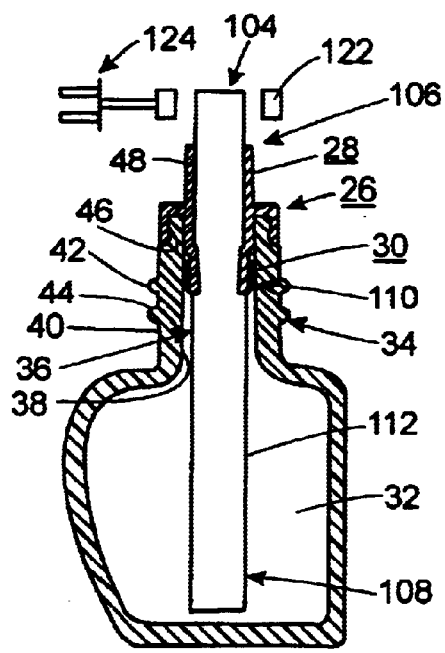
FIG. 2 is a cross-sectional view of the bottle assembly of FIG. 1 taken along line 2—2.
Figure 3:
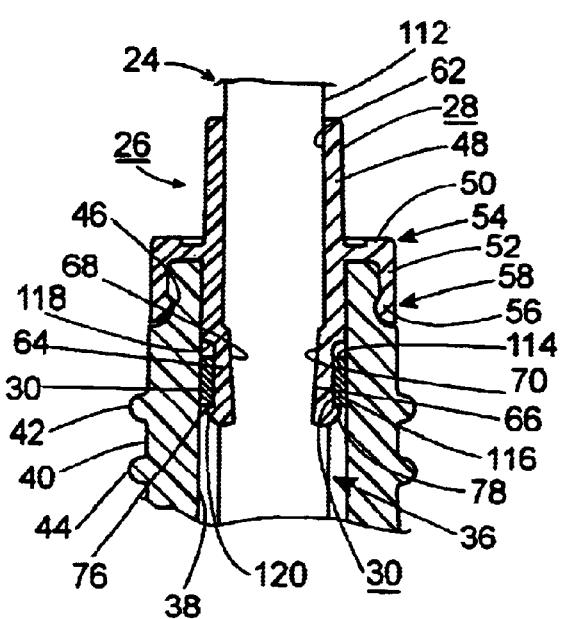
FIG. 3 is an enlarged, partial cross-sectional view of the bottle assembly of FIG. 1 taken along line 2—2.
Figure 4:
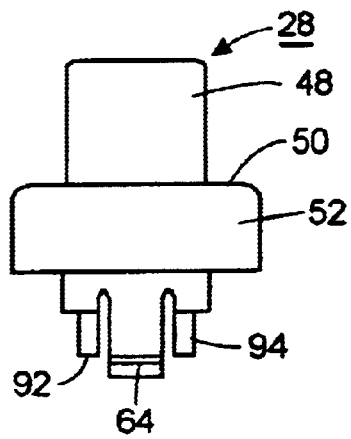
FIG. 4 is a side view of the wick holder shown in FIG. 1.
Figure 5:
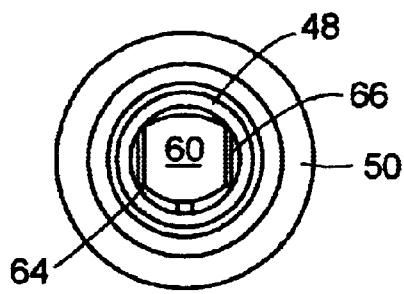
FIG. 5 is a top view of the wick holder of FIG. 4.

A bottle assembly 20 is shown in FIG. 1. The bottle assembly 20 may include a bottle 22, a wick 24, and a wick holder assembly 26. As shown in FIGS. 2 and 3, the wick holder assembly 26 may include a wick holder 28 and a clip 30.

As shown in FIGS. 1 and 2, the bottle 22 may include a reservoir 32 that may be filled with a fragrance solution that may include natural and/or synthetic fragrances and a carrier, as well as other constituents. The bottle also may include a neck 34 with a passage 36 therethrough in communication with the reservoir 32. The neck 34 may have an interior surface 38 that defines the passage 36.

The neck 34 may also have an outer surface 40 with threads 42, a latching rim 44, and wick holder retaining groove 46. The threads 42 may be used to secure a cap (not shown) to the bottle assembly 20 to prevent evaporation from the wick during storage. The latching rim 44 may be used to secure the bottle assembly 20 to a heater unit (not shown) such that the wick 24 is proximate to a heater. The wick holder retaining groove 46 may cooperate with the wick holder 28 as explained in greater detail below.

In particular, the wick holder 28 may include a central, cylindrical, tube-like section 48 with a flange 50 that depends radially outward from the central section 48. A skirt 52 may depend from the outermost edge 54 of the flange 50. A rib 56 may depend inwardly from the end 58 of the skirt 52. The rib 56 may be disposed in the wick holder retaining grove 46, such that movement of the wick holder assembly 26, and in particular the wick holder 28, may be limited.

The wick holder 28 may also have a wick holder passage 60 formed therethrough. The wick holder passage 60 may be defined in part by an inner surface 62 of the central section 48. The wick holder passage 60 may also be defined in part by two oppositely spaced fingers 64, 66, each of the fingers 64, 66 having an inner surface 68, 70 that defines in part the wick holder passage 60.

Each of the fingers 64, 66 may also have an outer surface 72, 74. The outer surfaces 72, 74 may each have a recess 76, 78 defined therein. In particular, each of the fingers 64, 66 may have a proximal section 80, 82 attached to the central section 48, a distal section 84, 86 which depends in a cantilevered fashion from the proximal section 80, 82, and an intermediate section 88, 90 that is between the proximal 80, 82 and distal sections 84, 86. As shown, the thickness of either of the intermediate sections 88, 90 is less than the thicknesses of the respective proximal 80, 82 and distal sections 84, 86.

Alternatively, the thickness of the intermediate section may be less that the distal sections 84, 86, but not the proximal sections 80, 82. In such a case, the proximal 80, 82 and intermediate sections 88, 90 may define the recesses 76, 78. As a further alternative, the thickness of the intermediate sections 88, 90 may be greater than that of the proximal section 80, 82, but may be less than, greater than or equal to that of the distal sections 84, 86. In this case, the proximal sections 80, 82 may define the recesses 76, 78. In addition, it may be that the proximal 80, 82, distal 84, 86 and intermediate sections 88, 90 are all of approximately equal thickness, in which case no recess is defined in the outer surface 72, 74 of either finger 64, 66.

While only two fingers 64, 66 have been shown, it will be recognized that the wick holder 60 may include any number of fingers, e.g., three, four, five, etc. Moreover, while the fingers 64, 66 as shown are disposed opposite of each other across the wick holder passage 60, the fingers 64, 66 need not be so symmetrically disposed. Asymmetries may occur, for example, when an odd number of fingers are used, rather than an even number.

Figure 6:
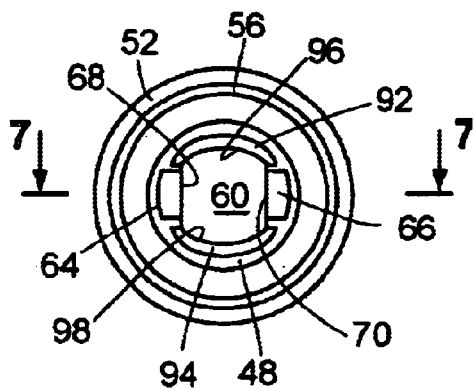
FIG. 6 is a bottom view of the wick holder of FIG. 4.
Figure 7:
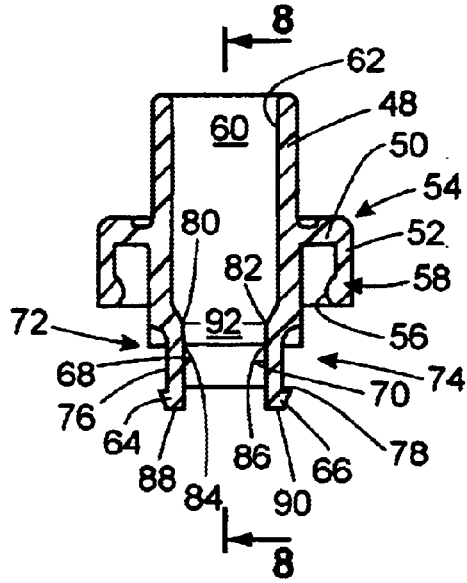
FIG. 7 is a cross-sectional view of the wick holder of FIG. 6 taken along line 7—7.
Figure 8:
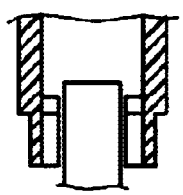
FIG. 8 is a partial cross-sectional view of the wick holder of FIG. 7 taken along line 8—8.

The wick holder 28 may also have two guides 92, 94 that depend from the central section 48 like the fingers 64, 66. Also like the fingers 64, 66, the guides 92, 94 may have inner surfaces 96, 98 that define in part the wick holder passage 60. The guides 92, 94 may be semi-circular or arcuate in cross-section, as seen best in FIG. 6. The dimension of the guides 92, 94 in the axial direction may not be as long as the fingers 64, 66, as shown in the Figures. Moreover, the position and thickness of the guides 92, 94 relative to that of the intermediate sections 88, 90 may be selected such that the guides 92, 94 do not interfere with the cooperation of the fingers 64, 66 and the clip 30.

As was the case with the fingers 64, 66, the number of guides 92, 94 shown is merely exemplary. The number of guides 92, 94 may be increased or decreased. For example, the guides 92, 94 may be removed. As a further alternative, if the number of fingers is increased to three, the number of guides may likewise be increased to three as well.

Figure 9:
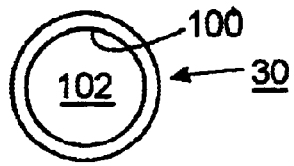
FIG. 9 is a top view of the clip shown in FIG. 1.

The clip 30, as shown in FIGS. 3 and 9, may have an annular, ring-like shape. The clip 30 has an inner surface 100 that defines a passage 102 therethrough. While the clip 30 shown is annular in shape, the clip 30 may alternatively have a C-shape or a U-shape.

To assemble the bottle assembly 20, a first end 104 of the wick 24 may be disposed through the wick holder passage 60, such that the first end 104 may depend from a first end 106 of the wick holder 28 and a second end 108 may depend from a second end 110 of the wick holder 28. The relative placement of wick 24 and wick holder 28 may be seen in FIG. 2, although at this point in the assembly, the clip 30 has not yet been disposed about the fingers 64, 66.

With the wick 24 in place, the fingers 64, 66 of the wick holder 28 and the second end 108 of the wick 24 are disposed through the passage 102 in the clip 30. The fingers 64, 66, and in particular the distal sections 84, 86, may be forced radially inward in the direction of an outer surface 112 of the wick 24 as the fingers 64, 66 and wick 24 are advanced through the passage 102 of the clip 30. Once the distal sections 84, 86 of the fingers 64, 66 have passed through the passage 102 of the clip 30, the fingers 64, 66 may return at least partially radially outwardly. Cooperation between shoulders 114, 116 of the clip 30 and shoulders 118, 120 defined by the proximal 80, 82, distal 84, 86 and intermediate sections 88, 90 of the wick holder 28 may limit the movement of the clip 30 relative to the wick holder 28 (see FIG. 3).

With the clip 30 disposed about the fingers 64, 66, the inner surface 100 of the clip 30 abuts the outer surfaces 72, 74 of the fingers 64, 66. In turn, the inner surfaces 68, 70 of the fingers 64, 66 abut the outer surface 112 of the wick 24. Moreover, the, fingers 64, 66 may be inwardly directed into the wick 24 by the cooperation of the clip 30 and the fingers 64, 66.

With the clip in place, the wick holder assembly 26 and wick 24 may be disposed into the passage 36 in the neck 34 of the bottle 22. The wick holder 28, and in particular the central section 48 of the wick holder 28, may be sized such that the outer effective diameter of the wick holder 28 is slightly greater than the effective diameter of the neck passage 36. In this case, the wick holder assembly 26 and wick 24 may be held in place, at least in part, by friction between the wick holder 28 and the inner surface 38 of the neck 34.

However, whether the wick holder 28 and the neck 34 form a tight interference fit, the movement of the wick holder assembly 26 relative to the bottle 22 may be limited through the cooperation of the wick holder retaining groove 46 and the rib 56. That is, with the wick holder assembly 26 and the wick 24 disposed in the passage 36 of the neck 34 of the bottle 22, the rib 56 may be disposed in the wick holder retaining groove 46. As stated above, the cooperation of these elements limits relative motion between the wick holder assembly 26 and the bottle 22.

Thus assembled, the bottle assembly 20 may be ready for use or storage.

In use, the bottle assembly 20 may be disposed such that the first end 104 of the wick is disposed relative to a heater unit 122 of a fragrance dispersal device (FIG. 2). The heater unit 122 may be coupled to a plug 124, for example a two or three-prong plug, as commonly used with electric outlets. In fact, the bottle assembly 20 and heater unit 122 may be attached via a housing (not shown) such that the bottle assembly 20, heater unit 122, and housing depend in cantilevered fashion with the plug 124 inserted into an electric outlet.

As the heater unit 122 evaporates the solution disposed at the end 104 of the wick 24, more fluid is drawn up through the wick 24 from the second end 108 that is disposed in the reservoir 32. After this fashion, fragrance is dispersed. Alternatively, a fan or other dispersal device may be used to disperse fragrance from the wick 24 into the surrounding environment. As a further alternative, the fragrance is permitted to evaporate from the wick 24 without the use of a dispersal device, such as a heater, fan or the like.

For storage, a cap (not shown) is disposed over the end 104 of the wick 24 and secured to the bottle assembly 20 utilizing the threads 42 on the outer surface 40 of the neck 34.

Although certain example apparatus and methods have been disclosed and described herein, the scope of coverage of this patent is not limited thereto. On the contrary, this patent covers all embodiments of the teachings of the invention fairly falling within the scope of the appended claims, either literally or under the doctrine of equivalents.

I claim:

1. A bottle assembly comprising:
   a bottle having a neck with a neck passage disposed therethrough;
   a wick holder assembly disposed in the neck passage and having a wick holder passage disposed therethrough,
   the wick holder assembly including at least two fingers, each of the fingers having an inner surface that defines part of the wick holder passage and an outer surface, and a clip disposed abutting the outer surfaces of the at least two fingers; and
   a wick disposed in the wick holder passage with at least a part of the wick between the at least two fingers,
   the wick having an outer surface that abuts the inner surface of the wick holder passage with the clip disposed abutting the outer surfaces of the at least two fingers.

2. The bottle assembly according to claim 1, wherein:
   the wick holder assembly includes two fingers disposed opposite each other across the wick holder passage.

3. The bottle assembly according to claim 2, wherein:
   the clip has an inner surface defining a clip passage therethrough, the inner surface of the clip abutting the outer surfaces of the at least two fingers with the at least two fingers disposed in the clip passage.

4. The bottle assembly according to claim 3, wherein:
   the clip comprises an annular ring.

5. The bottle assembly according to claim 3, wherein:
   each of the at least two fingers has a recess defined in the outer surface thereof, and
   the inner surface of the clip abutting the outer surface of the at least two fingers is disposed in the recess in each of the at least two fingers.

6. The bottle assembly according to claim 3, wherein:
   the wick holder comprises a tube-like section having a first end and a second end, the tube-like passage defining the wick holder passage in part, and
   the at least two fingers depending from the second end of the wick holder.

7. The bottle assembly according to claim 6, wherein:
   the wick holder comprises a flange, the flange depending from the first end of the tube-like passage and having a rib attached thereto, and
   the neck of the bottle has an outer surface with a groove defined therein, the rib disposed in the groove with the wick holder disposed in the neck passage.

8. The bottle assembly according to claim 7, wherein:
   the wick holder comprises a skirt attached to the flange, the skirt having the rib defined thereon.

9. The bottle assembly according to claim 1, wherein:

the bottle comprises a reservoir, and the wick has a first end depending from the wick holder outside the bottle and a second end disposed in the reservoir.

10. The bottle assembly according to claim 9, wherein:

a fragrance solution is disposed in the reservoir.

11. A bottle assembly comprising:

a bottle having a neck with a neck passage disposed therethrough, a wick holder assembly disposed in the neck passage and having a wick holder passage disposed therethrough, the wick holder assembly including at least two fingers, each of the fingers having an inner surface that defines part of the wick holder passage and an outer surface, and a clip disposed abutting the outer surfaces of the at least two fingers;

each of the at least two fingers having a section of lesser thickness disposed between two sections of greater thickness, the sections collectively defining a recess in each of the at least two fingers and the portion of the clip abutting the outer surface of the at least two fingers disposed in the recess in each of the at least two fingers; and a wick disposed in the wick holder passage with at least a part of the wick between the at least two fingers, the Wick having an outer surface that abuts the inner surface of the wick holder passage with the clip disposed abutting the outer surfaces of the at least two fingers.

12. A fragrance dispersal device comprising:

a bottle assembly including:

a bottle having a neck with a neck passage disposed therethrough;

a wick holder assembly disposed in the neck passage and having a wick holder passage disposed therethrough, the wick holder assembly including at least two fingers, each of the fingers having an inner surface that defines part of the wick holder passage and an outer surface, and a clip disposed abutting the outer surfaces of the at least two fingers; and a wick having a first end, a second end and an outer surface, the wick disposed in the wick holder passage with the first end depending outside the bottle, at least a part of the wick between the at least two fingers and the outer surface abutting the inner surface of the wick holder passage with the clip disposed abutting the outer surfaces of the at least two fingers; and a heater unit disposed adjacent the first end of the wick.

13. The fragrance dispersal device according to claim 12, wherein:

the bottle comprises a reservoir, and the wick has the second end disposed in the reservoir.

14. The fragrance dispersal device according to claim 13, wherein:

a fragrance solution is disposed in the reservoir.

15. The fragrance dispersal device according to claim 12, further comprising:

a plug coupled to the heater unit.

16. The fragrance dispersal device according to claim 12, wherein:

the wick holder assembly includes two fingers disposed opposite each other across the wick holder passage, and the clip comprises a ring having an inner surface defining a clip passage therethrough, the inner surface of the ring abutting the outer surfaces of the two fingers with the two fingers disposed in the clip passage.

17. A fragrance dispersal device comprising:

a bottle assembly including;

a bottle having a neck with a neck passage disposed therethrough;

a wick holder assembly disposed in the neck passage and having a wick holder passage disposed therethrough, the wick holder assembly including at least two fingers, each of the fingers having an inner surface that defines part of the wick holder passage and an outer surface, and a clip disposed abutting the outer surfaces of the at least two fingers;

each of the two fingers having a section of lesser thickness disposed between two sections of greater thickness, the sections collectively defining a recess in each of the two fingers and the portion of the clip abutting the outer surface of the two fingers disposed in the recess in each of the two fingers; and a wick having a first end, a second end and an outer surface, the wick disposed in the wick holder passage with the first end depending outside the bottle, at least a part of the wick between the at least two fingers and the outer surface abutting the inner surface of the wick holder passage with the clip disposed abutting the outer surfaces of the at least two fingers; and a heater unit disposed adjacent the first end of the wick.

18. The fragrance dispersal device according to claim 17, wherein:

the wick holder comprises a tube-like section having a first end and a second end, the tube-like passage defining the wick holder passage in part, and the two fingers depend from the second end of the wick holder.

19. The fragrance dispersal device according to claim 18, wherein:

the wick holder comprises a flange, the flange depending from the first end of the tube-like passage and attached to a skirt having a rib defined thereon, and the neck of the bottle has an outer surface with a groove defined therein, the rib disposed in the groove with the wick holder disposed in the neck passage.

20. An assembly comprising:

a wick holder assembly having a wick holder passage disposed therethrough, the wick holder assembly including at least two fingers, each of the fingers having an inner surface that defines part of the wick holder passage and an outer surface, and a clip disposed abutting the outer surfaces of the at least two fingers; and a wick disposed in the wick holder passage with at least a part of the wick between the at least two fingers, the wick having an outer surface that abuts the inner surface of the wick holder passage with the clip disposed abutting the outer surfaces of the at least two fingers.

* * * * *

UNITED STATES PATENT AND TRADEMARK OFFICE
CERTIFICATE OF CORRECTION

PATENT NO. : 6,619,560 B1 Page 1 of 1
DATED : September 16, 2003
INVENTOR(S) : Yip Po Chun It is certified that error appears in the above-identified patent and that said Letters Patent is hereby corrected as shown below:

<u>Column 5,</u>
Line 20, cancel "Wick" and insert -- wick --.

Signed and Sealed this

Second Day of March, 2004

JON W. DUDAS
*Acting Director of the United States Patent and Trademark Office*